(12) United States Patent
Johnstone et al.

(10) Patent No.: US 7,842,091 B2
(45) Date of Patent: Nov. 30, 2010

(54) IMPLANTABLE REPLACEMENT JOINT

(75) Inventors: Alan John Johnstone, Aberdeen (GB); Duncan Eoin Thomson Shepherd, Aberdeen (GB)

(73) Assignees: Grampian University Hospitals NHS Trust, Aberdeen (GB); University of Aberdeen, Aberdeen (GB)

( * ) Notice: Subject to any disclaimer, the term of this patent is extended or adjusted under 35 U.S.C. 154(b) by 1539 days.

(21) Appl. No.: 10/525,446

(22) PCT Filed: Aug. 26, 2003

(86) PCT No.: PCT/GB03/03763

§ 371 (c)(1),
(2), (4) Date: Feb. 23, 2005

(87) PCT Pub. No.: WO2004/017861

PCT Pub. Date: Mar. 4, 2004

(65) Prior Publication Data

US 2006/0167559 A1 Jul. 27, 2006

(30) Foreign Application Priority Data

Aug. 24, 2002 (GB) .................................. 0219758.0

(51) Int. Cl.
*A61F 2/30* (2006.01)
(52) U.S. Cl. ............... 623/18.11; 623/13.12; 623/21.15
(58) Field of Classification Search ............... 623/18.11, 623/21.15
See application file for complete search history.

(56) References Cited

U.S. PATENT DOCUMENTS

| 3,462,765 | A |   | 8/1969  | Swanson ........................... 3/1 |
| 3,990,116 | A | * | 11/1976 | Fixel et al. ............... 623/23.41 |
| 4,304,011 | A |   | 12/1981 | Whelan, III ................... 3/1.91 |
| 4,307,473 | A |   | 12/1981 | Weber ........................... 3/1.91 |
| 4,462,120 | A |   | 7/1984  | Rambert et al. ............... 3/1.911 |
| 5,011,497 | A | * | 4/1991  | Persson et al. ........... 623/23.41 |
| 5,062,851 | A |   | 11/1991 | Branemark ................... 623/18 |
| 5,534,033 | A |   | 7/1996  | Simpson ....................... 623/18 |
| 5,683,466 | A | * | 11/1997 | Vitale ....................... 623/21.15 |
| 5,702,472 | A | * | 12/1997 | Huebner .................. 623/21.15 |

FOREIGN PATENT DOCUMENTS

| EP | 0 057 597 | 8/1982  |
| EP | 0 115 564 | 8/1984  |
| EP | 0 524 874 | 1/1993  |
| EP | 0 925 765 | 12/1997 |

(Continued)

OTHER PUBLICATIONS

Beevers, D.J., et al.: "Metacarpophalengeal Joint Prostheses: A Review of Past and Current Designs." Proceedings of the Institution of Mechanical Engineers. Journal of Engineering in Medicine. Part H, Mechanical Engineering Publications Ltd., London, Great Britain.

*Primary Examiner*—Corrinne M McDermott
*Assistant Examiner*—Christopher D Prone
(74) *Attorney, Agent, or Firm*—Drinker Biddle & Reath LLP

(57) ABSTRACT

An implantable replacement joint includes first and second components having respective bores, and a flexible member within a cavity formed by the respective bores.

26 Claims, 16 Drawing Sheets

FOREIGN PATENT DOCUMENTS

| | | |
|---|---|---|
| FR | 2 724 309 | 3/1996 |
| FR | 2724309 A1 * | 3/1996 |
| GB | 2 160 779 | 1/1986 |
| GB | 2 169 512 | 7/1986 |
| WO | WO 84/04668 | 12/1984 |
| WO | WO 91/16014 | 10/1991 |
| WO | WO 94/13228 | 6/1994 |

* cited by examiner

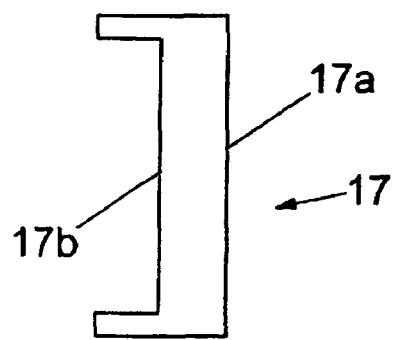
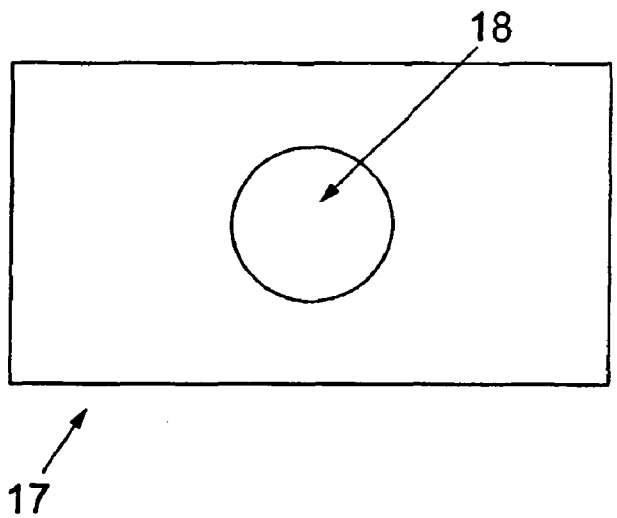
Fig. 7
Fig. 8

IMPLANTABLE REPLACEMENT JOINT

This Application is the U.S. National Phase Application of PCT International Application No. PCT/GB2003/003763 filed Aug. 26, 2003.

This invention relates to an implantable replacement joint, preferably but not limited to a body-implantable replacement joint to replace worn or damaged joints in a body.

DESCRIPTION OF THE RELATED ART

Joint replacement is a well established practice for treating patients suffering from diseases such as inflammatory arthritis or osteoarthritis. These conditions can result in considerable pain, loss of function, deformity and loss of quality of life. The most common types of artificial implant joints are used to replace worn or damaged hip joints, and typically consist of a ball and socket arrangement attached to bones at respective sides of the joint, or flexible silicon-based bridges such as the Swanson device, which is used for smaller joints such as the wrist or fingers. Loosening, dislocation tearing and fracture have been all reported for existing implants.

BRIEF SUMMARY OF THE INVENTION

According to the present invention there is provided an implantable replacement joint comprising a first component for attachment to a first bone portion; a second component for attachment to a second bone portion; and a flexible component extending between the first and second components; wherein each of the first and second components has a respective bore and the flexible component is received within a cavity formed by the bores of the first and second components; and wherein the flexible component is freely-floating within the cavity.

The first bone portion is typically located on one side of a joint, and the second bone portion is typically located on the other side of the joint.

The first and second components are typically adapted to be anchored within cavities in the respective first and second bone portions on opposing sides of the joint to be replaced. The first and second components can typically be anchored in place using friction, and in such embodiments can be shaped to be an interference fit within a cavity of the first and second bone portions. The cavity can be naturally occurring, e.g. the intramedullary canal, or can be created within a bone or group of bones to receive the first and second components, as required. In alternative embodiments, the first and second components can be anchored into the respective bone portions using adhesives, cement, grout, screw threads, or fixing devices such as screws, nails or expansion devices etc.

In certain embodiments the first and second components have formations on their outer surfaces in order to key into the inner surfaces of the cavities in the first and second bone portions. The formations on the outer surfaces of the first and second portions can typically be screw threads, annular or semi-annular ridges or simple protrusions or expansion fins on the outer surfaces.

Typically the flexible component is elongate. In preferred embodiments, each of the first and second components has an elongate stem with a central bore extending along the stem to receive a part, e.g. one end, of the flexible component. In such embodiments, the flexible component can thus be substantially contained within a cavity formed by the central bores of the first and second components. Typically the cavity is longer than the flexible component, so that the flexible component can move axially within the cavity. Typically the bores of the first and second components are wider than the flexible component so that the flexible component is a loose fit within the cavity. The relative dimensions of the flexible component and the first and second components are preferably such that even if the first and second components are pushed together to close any gap between the central bores, the flexible component will not be compressed within the cavity by the first and second components.

In especially preferred embodiments, the first and second components have bearing surfaces that articulate against one another when the device is made up. Typically the central bores and the flexible component extend through the bearing surfaces. The bearing surfaces can be arcuate and can be adapted to promote pivotal movements of the first and second components relative to one another. Preferably bearing surfaces promote particular pivotal movements e.g. in a particular plane. Typically the arcuate portions of the respective bearing surfaces on the first and second components are arranged on opposite axes, so that, for example, the bearing surface on the first component can be convex along an x-axis, and the bearing surface on the second component can be convex along a y-axis intersecting the x-axis. This arrangement can be extremely useful in promoting pivotal movements in more than one plane, allowing the replacement joint a number of degrees of freedom of movement, while controlling the location of the pivot axis on the device. However, it is envisaged that simple embodiments of the invention can be created with only one degree of freedom of movement, and without curved bearing surfaces.

Typically the first and second components are made from a relatively hard plastics material or carbon fibre composites, and preferably from one that is not biodegradable. Suitable materials for the first and second components include stainless steel, alloys such as cobalt chrome or titanium alloy, polyethylene or other plastics materials, or ceramics or carbon fibre composites. It can be advantageous to use materials for the first and second components that have a similar modulus to bone itself, and plastics materials are particularly useful in this respect.

The flexible component can be made from a resilient material such as rubber, and in preferred embodiments of the invention, the flexible component does have some resilience. The flexible component is typically formed from a relatively softer material than the first and second components. The flexible component can be made from e.g. silicone or polyurethane and can preferably have a flexibility that is intrinsic to the material used, although other forms of flexible component can be used where the flexibility is derived from e.g. a hinge inserted into a rigid material. The material chosen for the flexible portion is typically different from the material chosen for the first and second portions.

The flexible portion can typically have a convoluted hinge made up from a convoluted or folded section of the material.

In some embodiments of the invention, a bearing plate can be provided between the bearing surfaces of the first and second components. The bearing plate can typically be of a different material from the first and second components (for example, where the first and second portions are made from plastics material, the bearing plate can usefully be made from a metal), in order to reduce wear caused by the bearing surfaces of the first and second components rubbing against one another.

Embodiments including a bearing plate are especially advantageous where the joint being replaced has to bear significant loads e.g. wrist joints. In such cases, the first and second components are typically formed from a plastics material and the bearing plate 17 is preferably formed from a metal (e.g. stainless steel or titanium) or ceramics, which provide a low-friction interface between the bearing plate 17 and each of the first and second components. Replacement joints which do not have to bear such significant loads, such as replacement finger joints may be formed with or without bearing plate 17.

The bearing plate can have arcuate surfaces if desired, but in simple embodiments has generally flat faces. The bearing plate can extend the range of movement that is possible between the first and second components, by introducing an additional pivot point, so that each of the first and second components pivots on opposite faces of the bearing plate. The bearing plate can be formed with legs, extensions or prominent edges that can generally attach the bearing plate to one of the first and second components. The bearing plate could also be formed of plastics material, ceramics or other suitable materials. Where the first and second components are formed from ceramics materials, the bearing plate can comprise a plastics material so as to provide an interface of different materials at the bearing surfaces.

The replacement joint of the invention is preferably a wrist joint, but can also be used in any joint, particularly fingers, toes, knees and elbows. Is particularly useful to replace worn or damaged joints where more than two degrees of freedom is required, such as rotation of the first and second components in addition to flexion/extension and medial/lateral deviation.

In especially preferred embodiments of the invention, the pivot axis around which the first and second components move relative to one another is typically movable relative to the device, and this is typically achieved by the ability of the flexible component to move within the bores of the first and second components, thereby creating a "sloppy hinge" between the first and second components. This permits the first and second components to move axially relative to one another while moving in relative rotation and flexion/extension or in medial/lateral directions. Indeed, the ability to move axially while rotating, deviating laterally, and flexing or extending enables the replacement joint to move in a similar fashion to the natural joint it is replacing. This reduces strain on the anchoring points between the bone portions and the first and second components, and reduces pull-out failures or bone wear at the interfaces.

BRIEF DESCRIPTION OF THE SEVERAL VIEWS OF THE DRAWINGS

An embodiment of the present invention will now be described by way of example, and with reference to the accompanying drawings, in which;

FIG. 7 is a side view of a bearing plate used in the FIG. 1 device;

FIG. 8 is a plan view of the bearing plate;

DETAILED DESCRIPTION OF THE INVENTION

Figure 1:
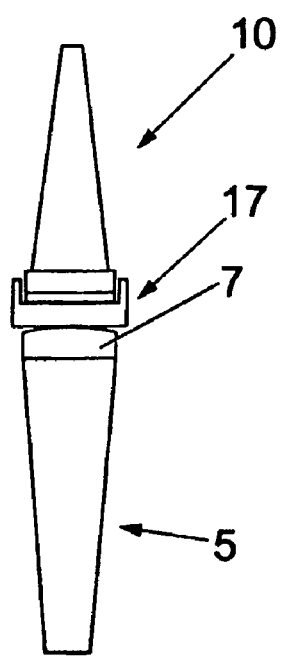
FIG. 1 is a side view of a body implantable device.

Referring now to the drawings, a body implantable device designed for use as the replacement wrist joint comprises a first component 5 and a second component 10. The first component 5 is dimensioned and adapted to be implanted within the distal end of the intramedullary canal of the radius, and the second component 10 is intended and adapted to be implanted into a bore created in the proximal part of the carpus and/or metacarpals. Each of the first and second components 5, 10 can have external protrusions such as ridges or screw-threads (not shown) to enhance retention of the component within the bone portion into which it is implanted. In this embodiment, each of the first and second components 5, 10 is sized and adapted to fit within either the intramedullary canal of the radius or the bore created in the carpus and/or metacarpals and to form an interference fit within that cavity, so that they can be retained therein merely by friction between the outer surface of the components 5, 10, and the inner surface of the cavity in the bone(s).

Figure 3:
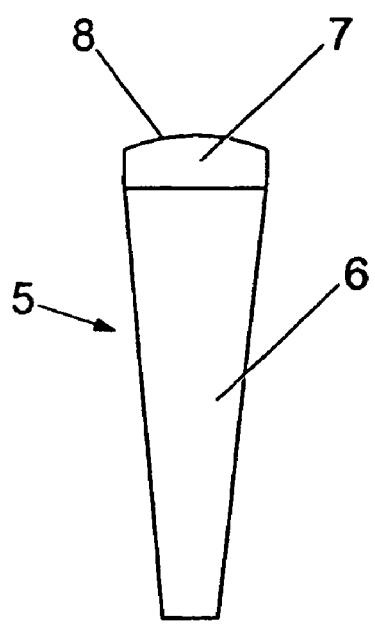
FIG. 3 is a side view of a first component of the FIG. 1 device.
Figure 4:
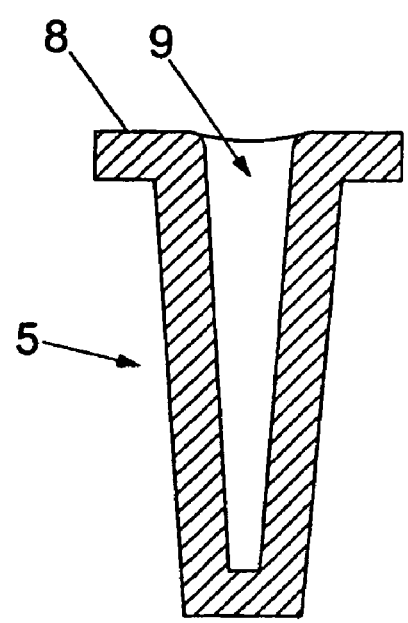
FIG. 4 is a front sectional view through the FIG. 3 component.

With reference to FIG. 3 and FIG. 4, the first component 5 comprises a tapered stem 6 adapted to fit within the distal intramedullary canal of the radius, and a head 7 located on top of the stem 6. The head 7 has laterally extending arms and has a distal convex bearing surface 8 that is curved from the front of the first component 5 to the back. The radius of curvature of the surface 8 is approximately 16 mm. The first component 5 has a blind-ended bore 9 extending axially through the stem 6, and presenting an aperture through the upper surface 8 of the head 7.

The first and second components are made from ultrahigh molecular weight polyethylene.

Figure 6:
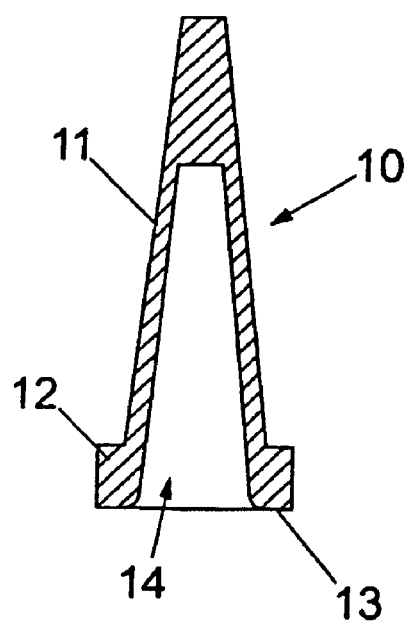
FIG. 6 is a side sectional view through the FIG. 5 component.
Figure 5:
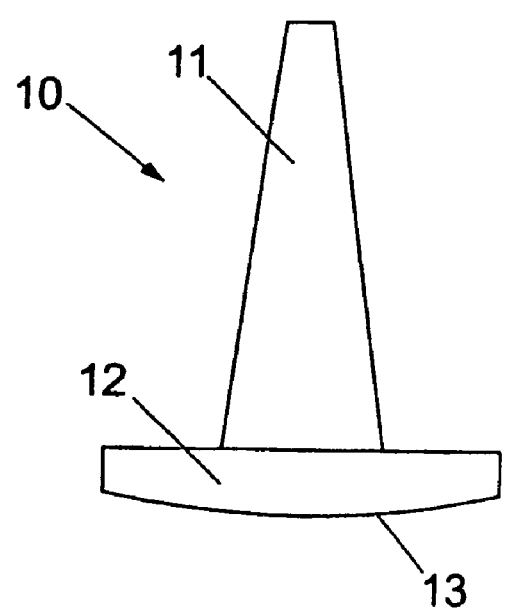
FIG. 5 is a front view of a second component of the FIG. 1 device.

With reference to FIGS. 5 and 6 the second component 10 also has a tapered stem 11, and a head 12, again with laterally extending arms, and a proximal bearing surface 13. The proximal bearing surface 13 of the head 12 is also convex, but is curved from one side of the second component 10 to the other side. The radius of curvature of the bearing face 13 is approximately 65 mm. The second component 10 has a blind-ended bore 14 extending axially through the stem 11, and presenting an aperture through the upper surface 13 of the head 12.

Figure 9:
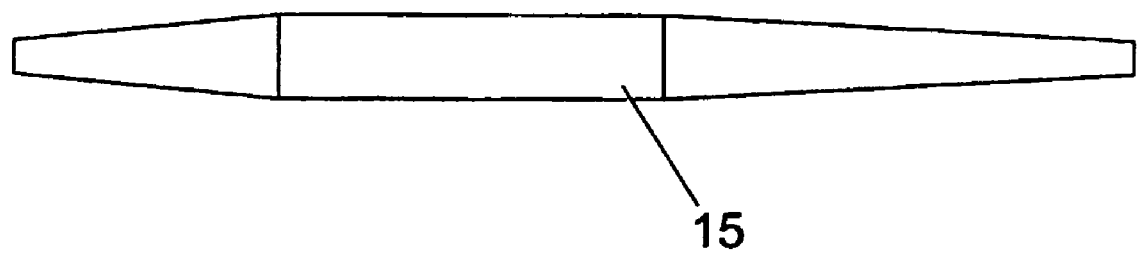
FIG. 9 is a side view of a flexible component of the FIG. 1 device.

A flexible rod 15 of silicone as shown in FIG. 9 has a central cylindrical portion and tapered ends that are adapted to be received within the blind ended bores 9, 14 of the first and second components 5, 10 respectively. The length of the flexible rod is typically slightly less than the combined lengths of the blind ended bores 9, 14, so that when the device is assembled with the first and second components 5, 10 placed head-to-head, with the bores 9, 14 aligned and the arms on the respective heads arranged parallel to one another, the flexible rod 15 can move axially within the cavity formed by the two bores 9, 14.

With reference to FIGS. 7 and 8, a bearing plate 17 formed of stainless steel is typically provided between the bearing surfaces 8, 13 of the heads 7, 12, and typically has an aperture 18 to allow passage of the flexible rod 15 through the bearing plate 17. The aperture 18 is aligned with the bores 9, 14 when the device is assembled. In this embodiment, the device is made up such that the bearing surface 8 of the first component 5 articulates against one surface 17a of the bearing plate 17, while the bearing surface 13 of the second component 10 articulates against the opposite surface 17b of the bearing plate 17. The bearing plate 17 typically has arms extending from the surface 17b plate to engage the side walls of the head 12 of the second portion 10. It will be appreciated that embodiments of the invention can function satisfactorily without a bearing plate 17, and that bearing plates can be used without side walls.

Figure 10:
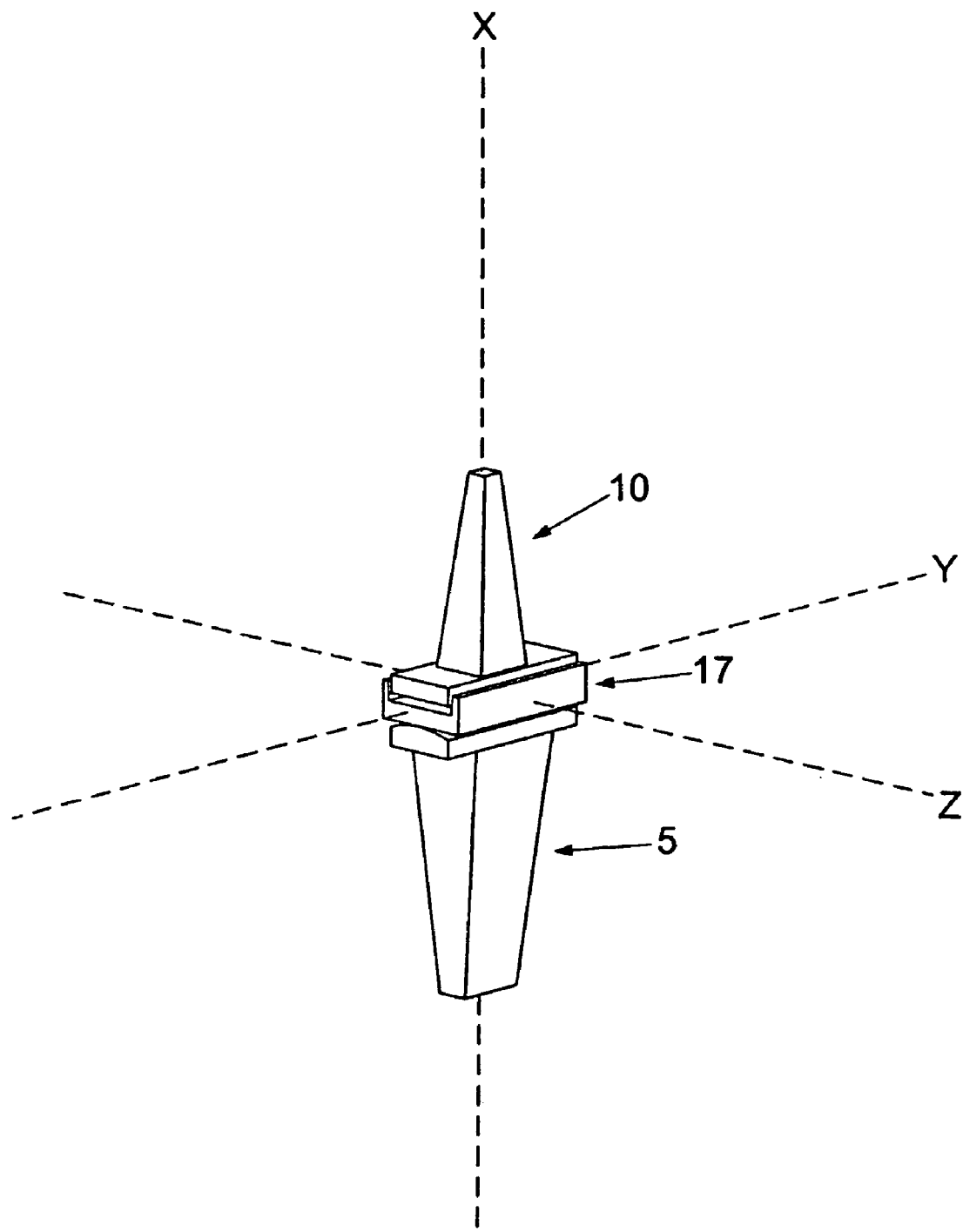
FIG. 10 is a perspective view of the FIG. 1 device.
Figure 11:
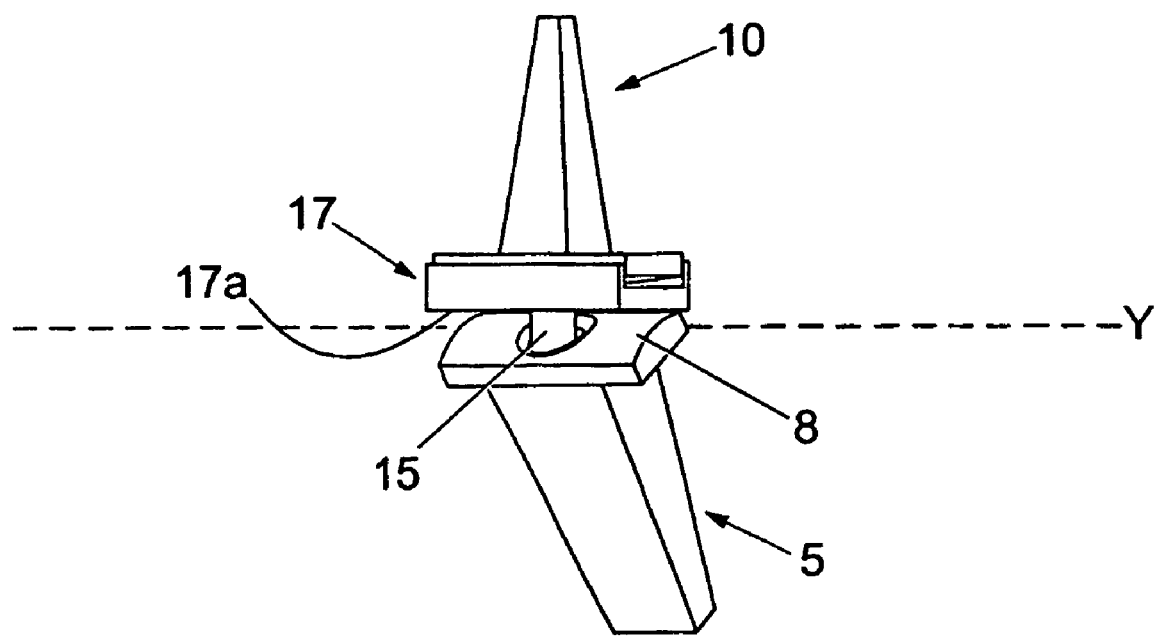
FIG. 11 is a perspective view of the FIG. 1 device in flexion/extension.
Figure 12:
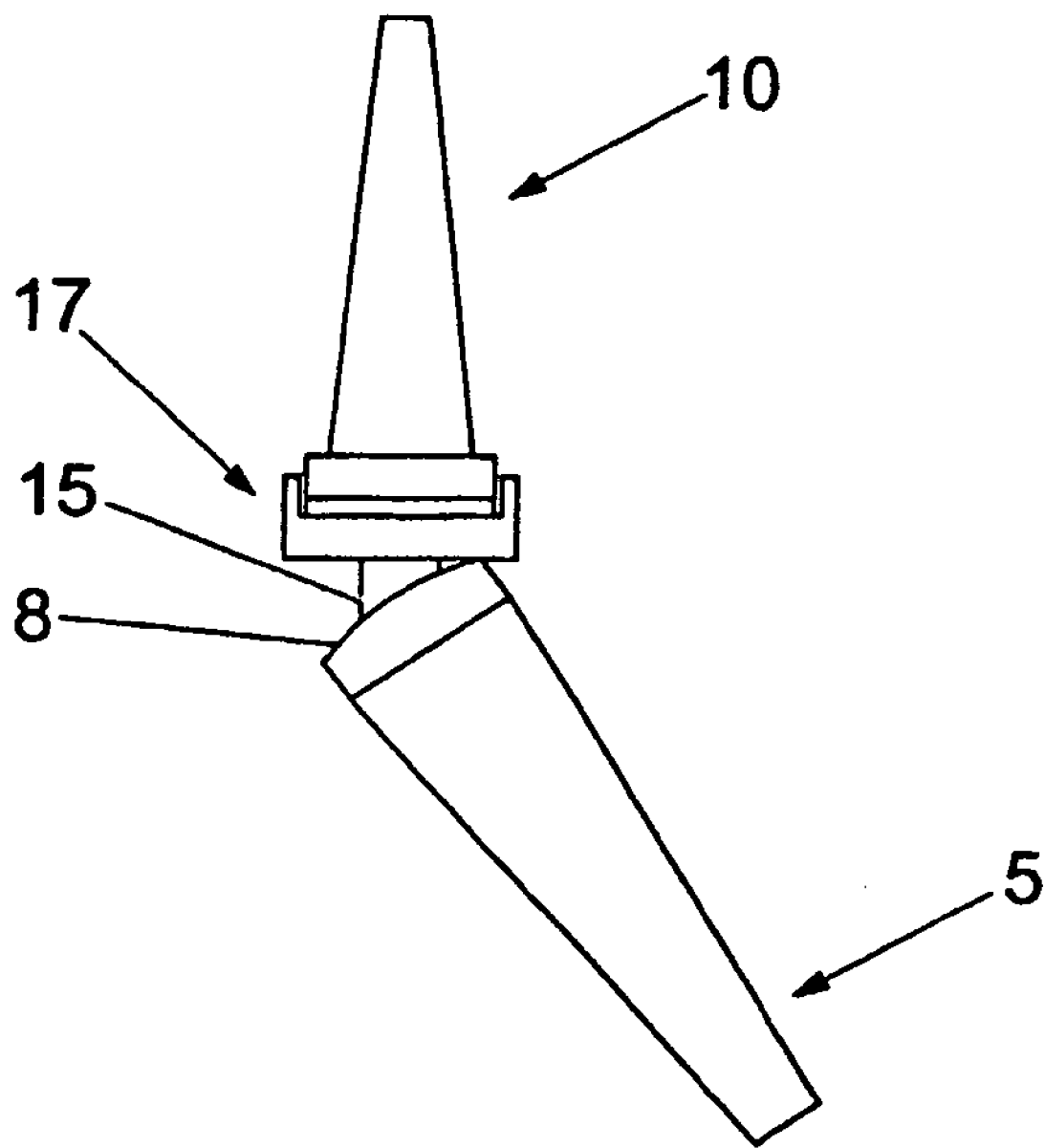
FIG. 12 is a side view of the FIG. 1 device in flexion/extension.

Turning now to FIGS. 10 to 17, the device is shown at rest in FIG. 10, with the two components 5, 10 in axial alignment with one another with the bearing plate 17 interposed. In this configuration, the flexible rod 15 is not bent or energised in any way and is held within the cavity formed by the bores 9, 14. FIGS. 11 and 12 show the device in flexion, with the second component 10 pivoting with respect to the first component 5 around the y-axis shown in FIG. 10. Notice that the bearing plate 17 moves with the second portion 10 relative to the first portion 5, and that the bearing surface 8 of the head 7 of the first portion 5 articulates against the face 17a of the bearing plate 17. The front to back curvature of the bearing surface 8 promotes a smooth articulation about the y-axis. The ends of the flexible rod 15 remain within the bores 9, 14, and the central portion of the rod 15 bends to accommodate and control the flexion. Since the rod 15 can move axially within the cavity formed by the bores 9, 14, the pivot axis formed in the central portion of the rod 15 can move axially with respect to the first and second portions 5, 10 as the device flexes, thereby allowing a greater range of movement of the joint. Also, since the flexible rod 15 can move within the cavity formed by the bores 9, 14, the two portions 5, 10 can extend relative to one another along the x-axis, while undergoing flexion, extension, medial/lateral deviation and/or rotation.

Figure 13:
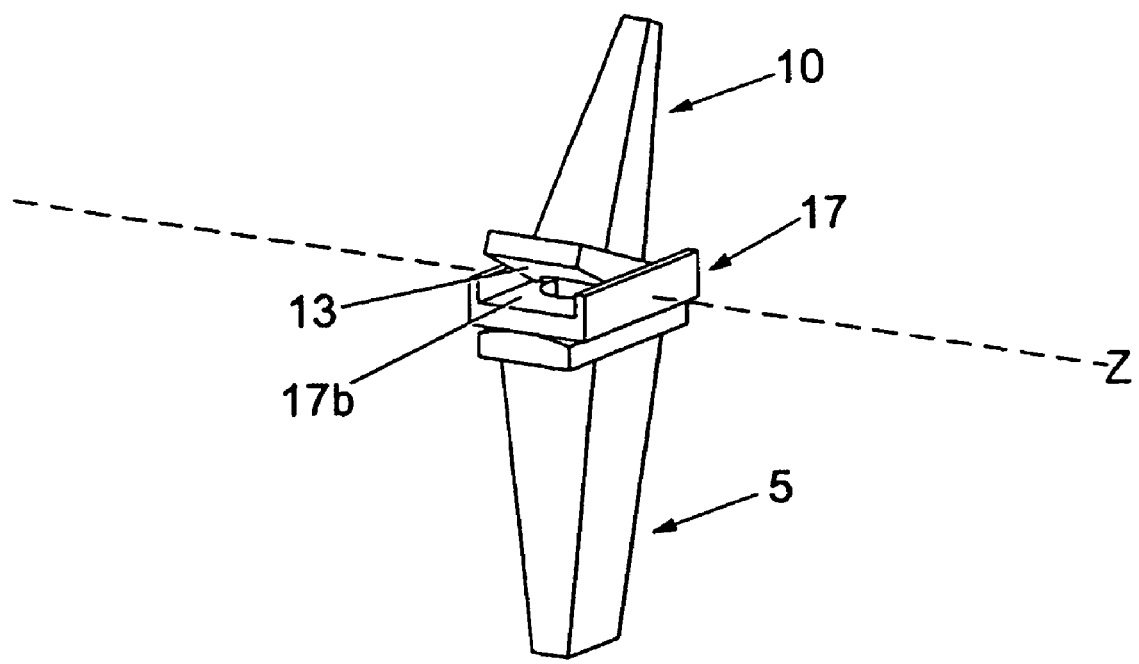
FIG. 13 is a perspective view of the FIG. 1 device showing lateral deviation.
Figure 14:
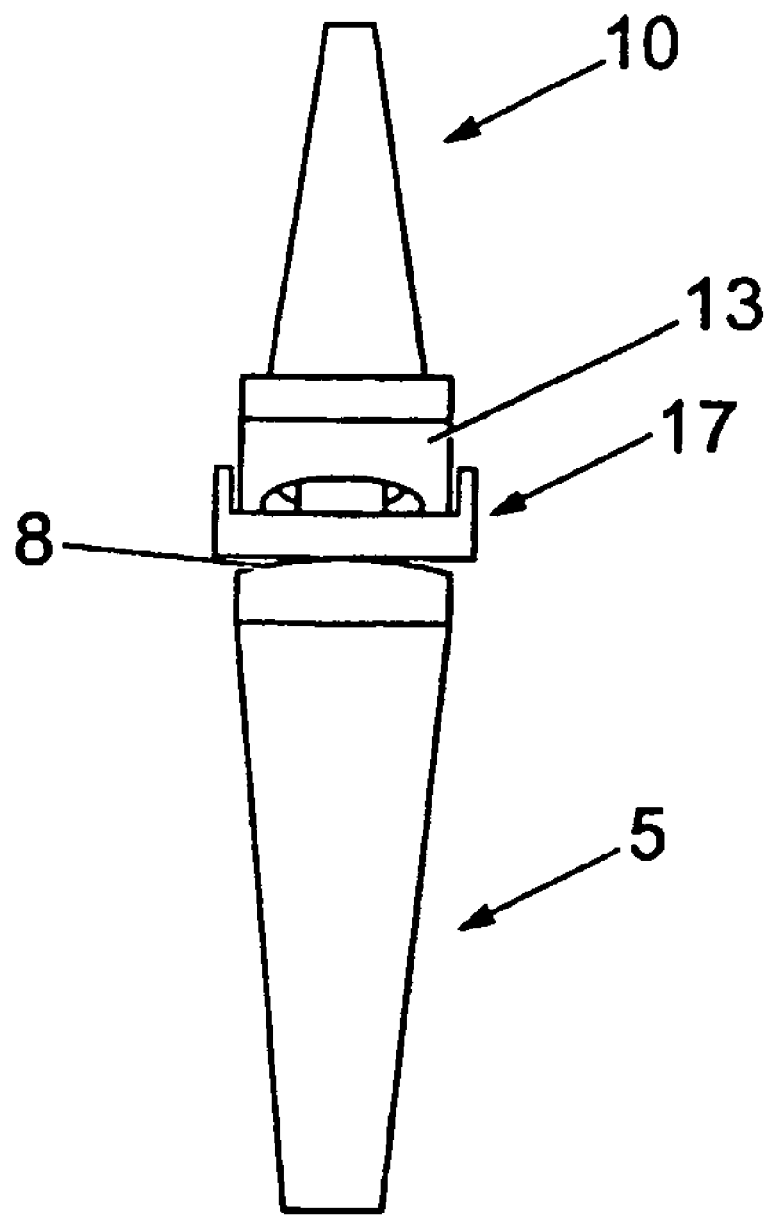
FIG. 14 is a side view of the FIG. 1 device showing lateral deviation.
Figure 15:
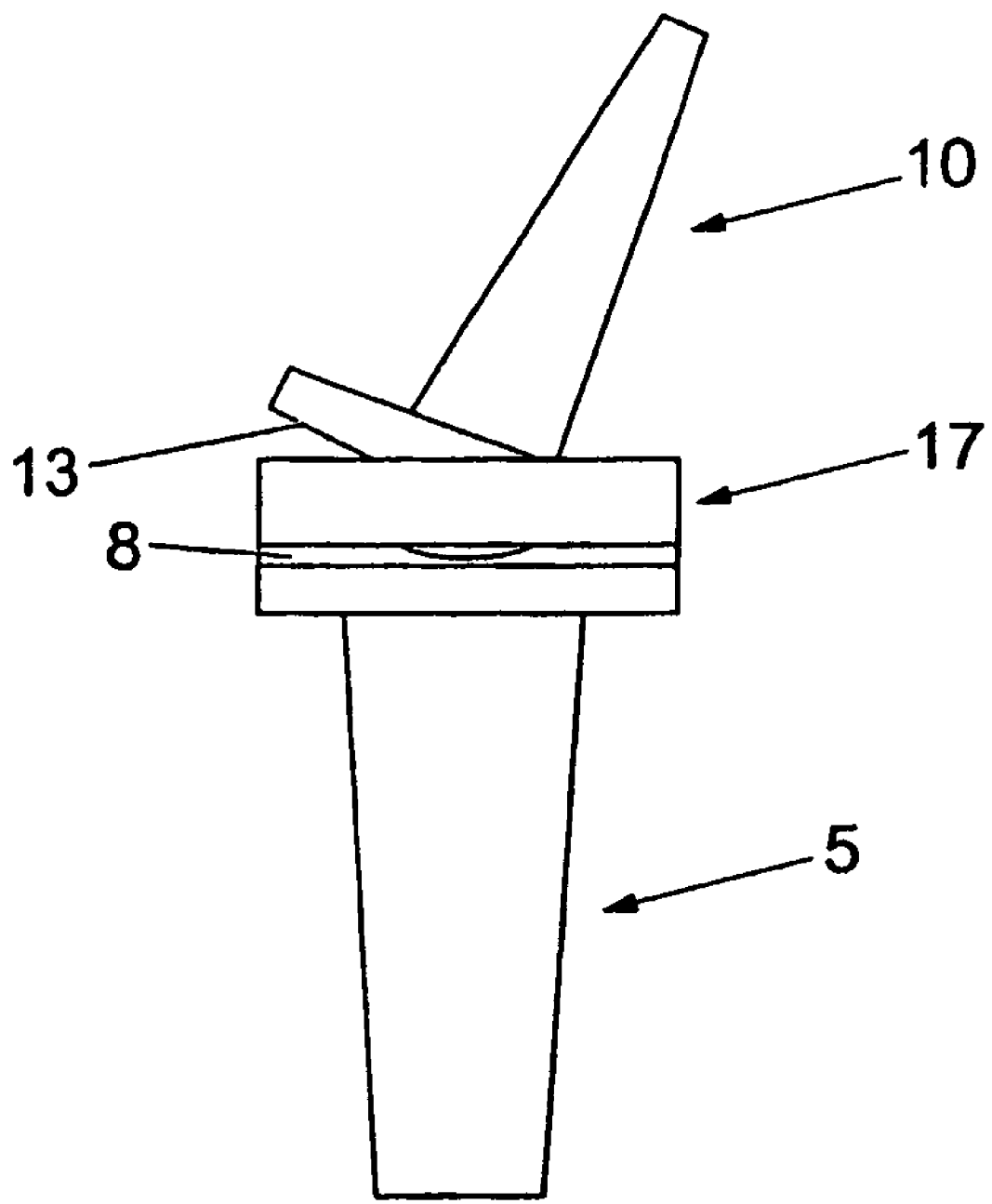
FIG. 15 is a front view of the FIG. 1 device showing lateral deviation.

FIGS. 13, 14 and 15 show the joint moving in medial/lateral deviation around the z-axis of FIG. 10, i.e. as if moving in radio-ulnar deviation when in place in the body. Notice that during lateral deviation around the z-axis, the bearing plate 17 remains with the first portion 5, and the bearing surface 13 of the head 12 of the second portion 10 articulates against the surface 17b of the plate 17. In pure lateral deviation, with no movement around the y-axis, the pivotal movement of the plate 17 relative to the first portion 5 is negligible, and the lateral movement of the first portion 10 is constrained by the head 12 moving within the confines of the arms of the bearing plate 17. In certain circumstances, the plate 17 can move relative to the first portion 5, for example, when the flexible rod 15 moves axially to allow the extension of the device.

Figure 16:
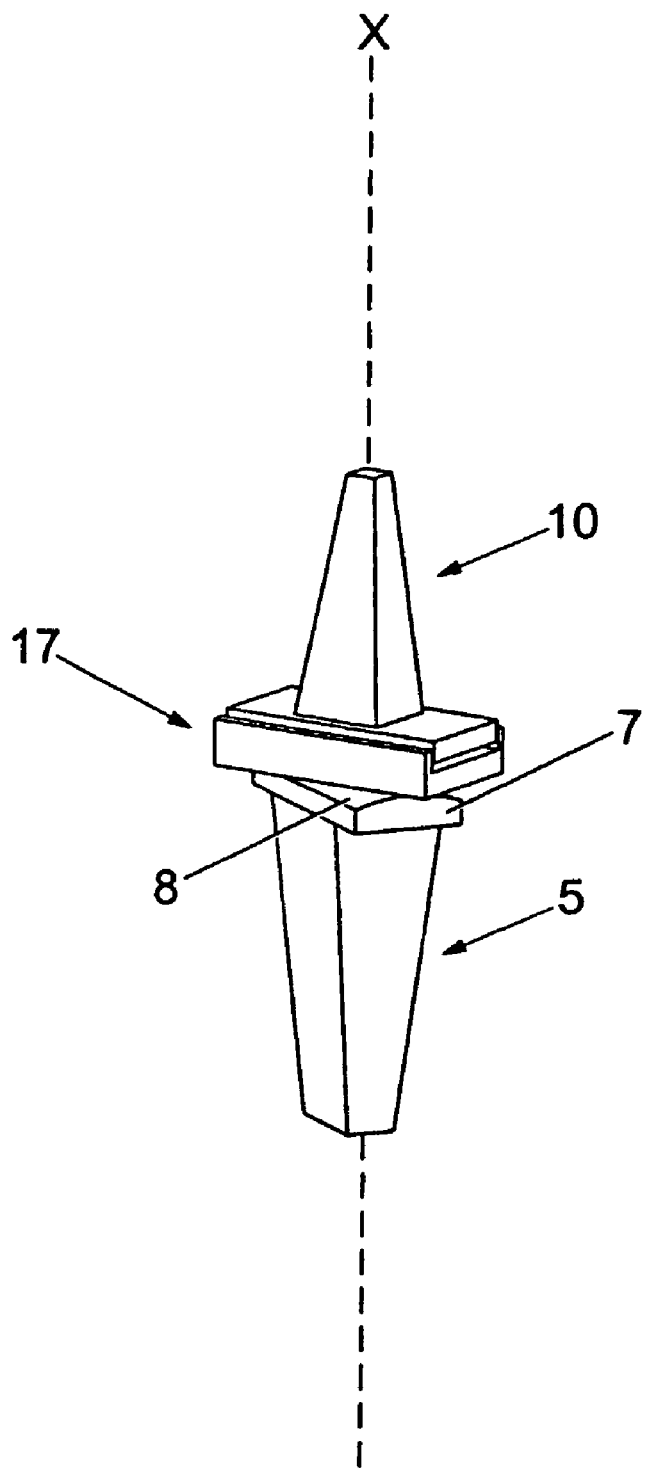
FIG. 16 is a perspective view of the FIG. 1 device showing relative rotation of the two components.
Figure 17:
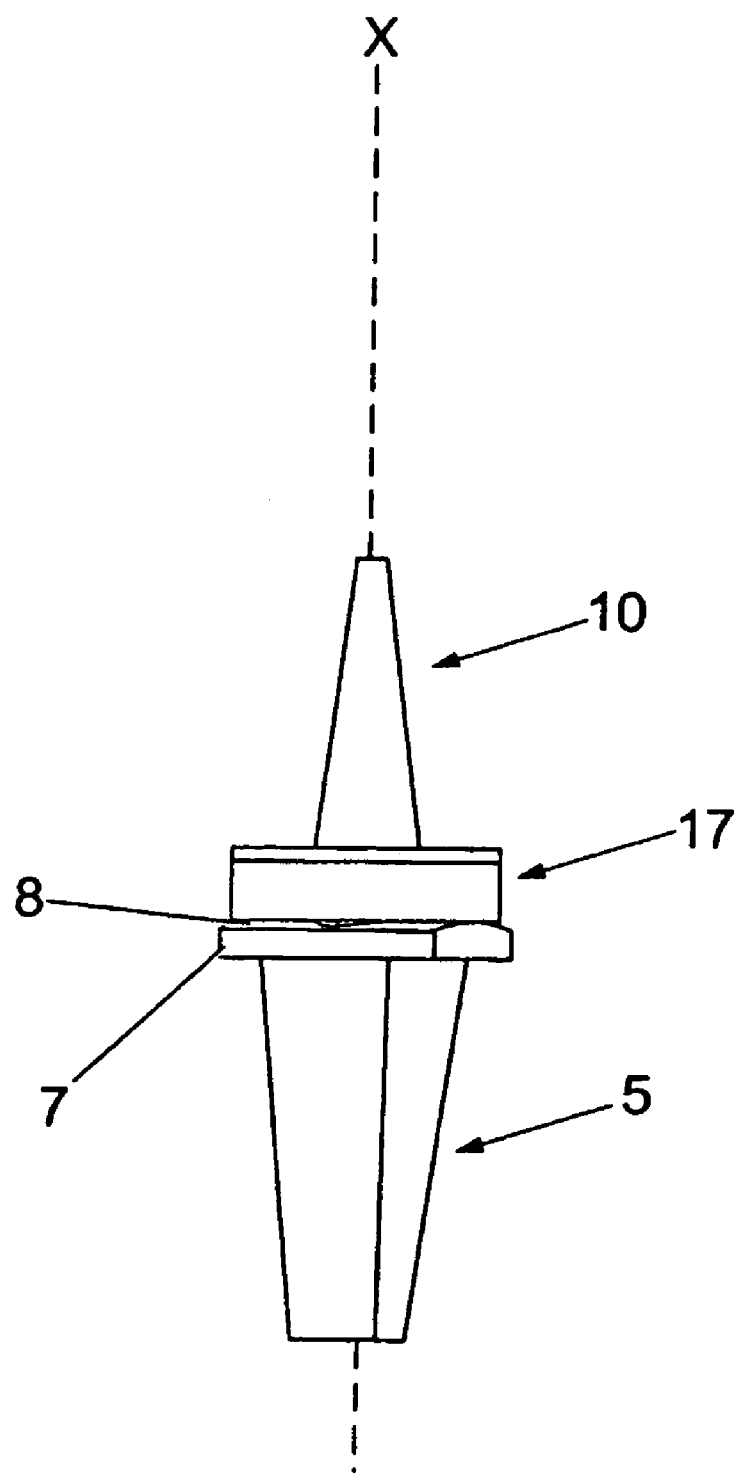
FIG. 17 is a side view of the FIG. 1 device showing relative rotation of the two components.

FIGS. 16 and 17 show relative rotational movement of the two portions 5, 10 around the x-axis. Notice that the arms of the bearing plate 17 keep the plate 17 stationary with respect to the second portion 10, and the two portions pivot around the axis of the flexible rod 15 held straight within the central cavity formed by the bores 9, 14.

Clearly it is possible for the joint to carry out more complex combination movements involving a combination of rotation, medial/lateral deviation, and extension/flexion, in any combination. It is also possible for axial separation of the two portions to occur during any such movement.

Figure 2:
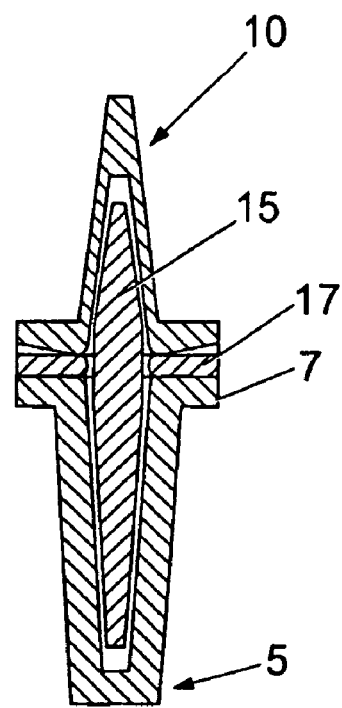
FIG. 2 is a front sectional view through the device of FIG. 1.
Figure 18:
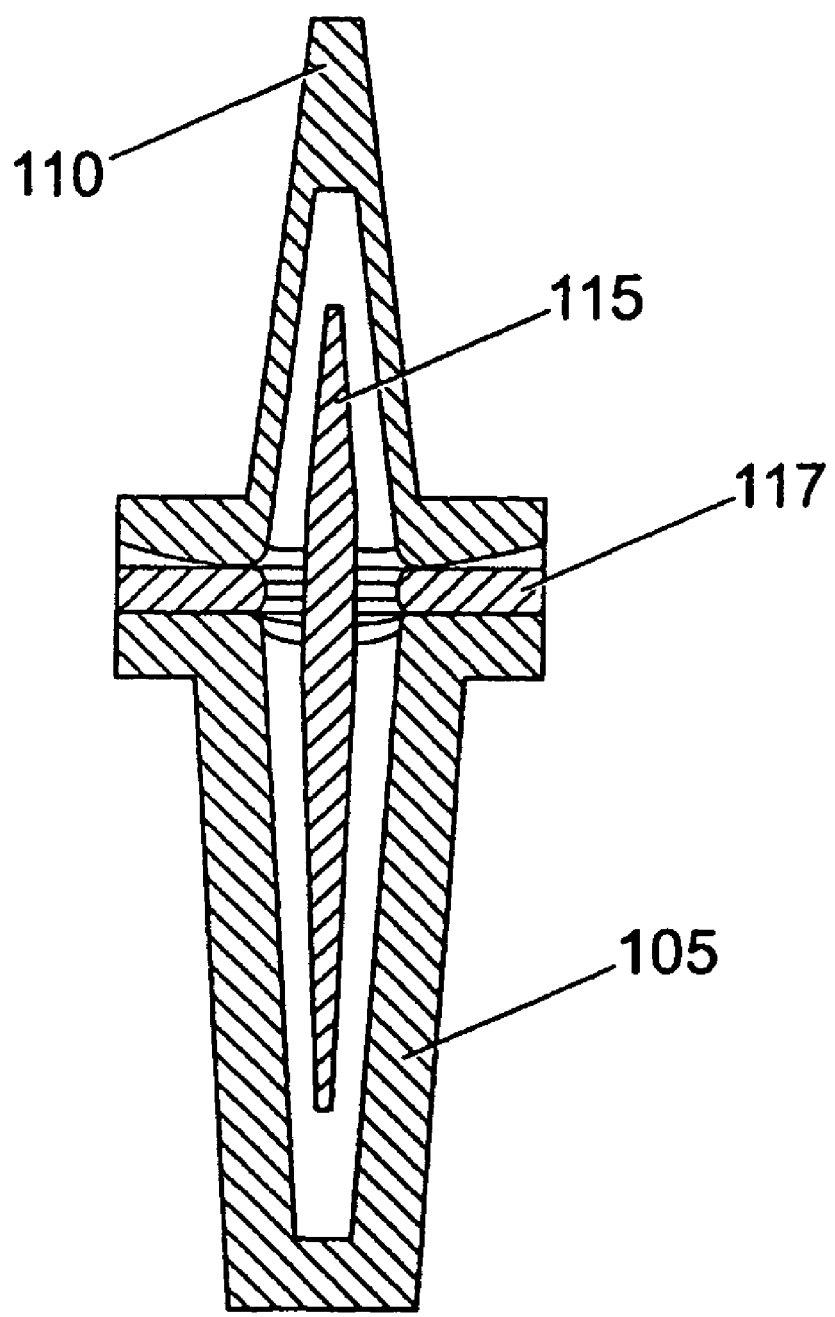
FIG. 18 is a front sectional view of an alternative embodiment of the invention.

Modifications and improvements can be incorporated without departing from the scope of the invention. For example, the flexible member does not need to have the tapered form shown in FIGS. 2 and 9; instead the flexible member could be an un-tapered cylinder or a coil spring. FIG. 18 shows an alternative embodiment, having a first component 105, a second component 110, a flexible member 115 and a bearing plate 117. Like the FIG. 1 embodiment, each of the first and second components 105, 110 and bearing plate 117 have a respective internal bore though which flexible member 115 extends. Both ends of the bore of flexible member 115 are chamfered, as are the mouths of the bores of the first and second components 105, 110; this is advantageous, as it means there are no sharp edges which could abrade and damage the flexible member 115.

The cavity formed by the bores in the first and second components 105, 110 is longer and wider than flexible member 115, providing clearance between flexible member 115 and the cavity in both axial and lateral directions. As flexible member 115 is not fixed to either of the first or second components 105, 110, flexible member 115 can move both axially, laterally and rotationally within the cavity; the flexible member thus has three degrees of freedom of movement.

Figure 19:
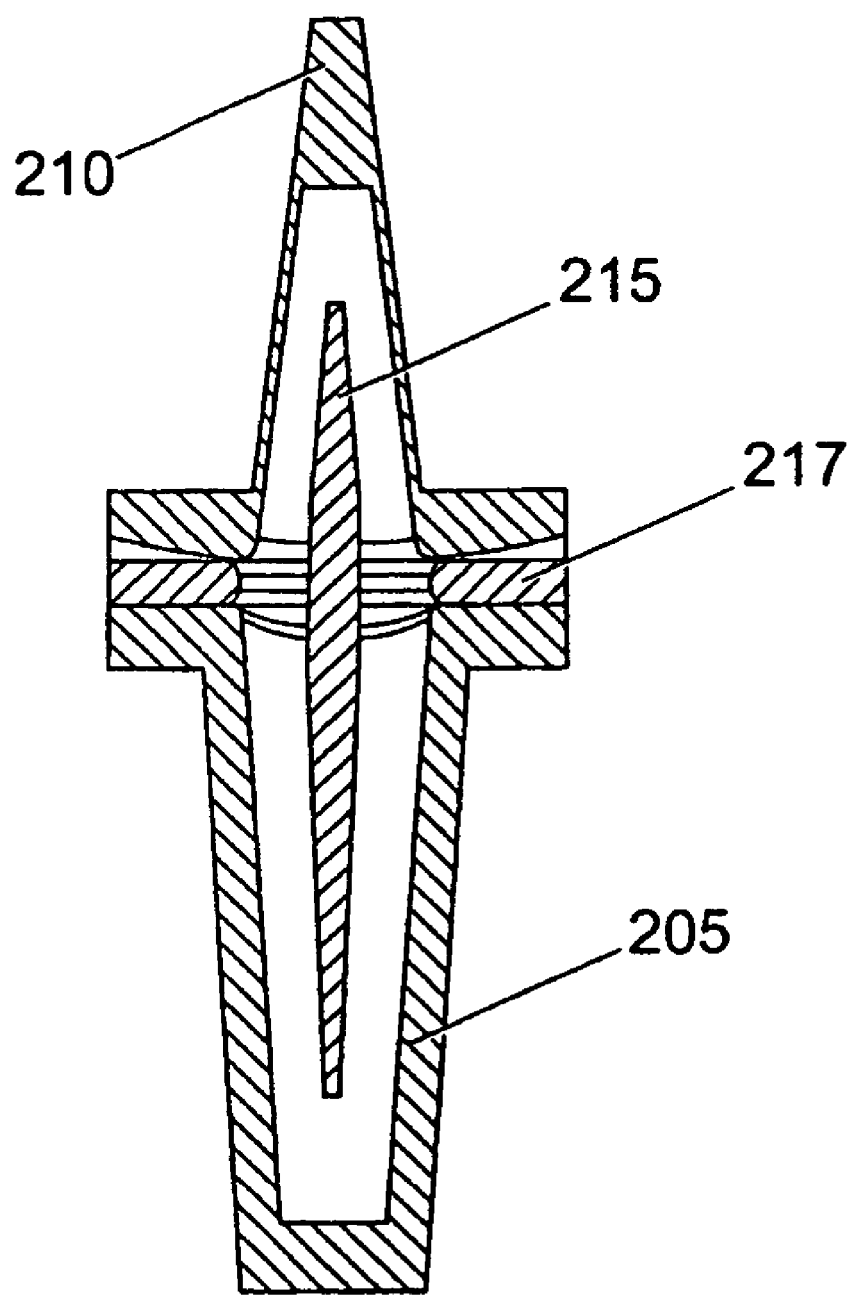
FIG. 19 is a front sectional view of a further alternative embodiment of the invention.

FIG. 19 shows a further embodiment of the invention which is very similar to the FIG. 18 embodiment and like components have similar reference numbers, which are prefixed by "2". The bores in the first and second components 205, 210 increase in width towards the respective bore mouths at a greater rate than the increase in diameter of the flexible member 215 due to its taper. This provides a greater clearance between flexible member 115 and the bores at the bore mouths compared to the bore ends.

The FIG. 19 embodiment has the advantage that stresses on the flexible member 215 are further reduced due to the relatively large clearance at the mouths of the bores in a first and second components 205, 210 and a correspondingly wide bore in flexible member 215.

It should be noted that the FIG. 18 and FIG. 19 embodiments are not necessarily drawn to scale.

Figure 20:
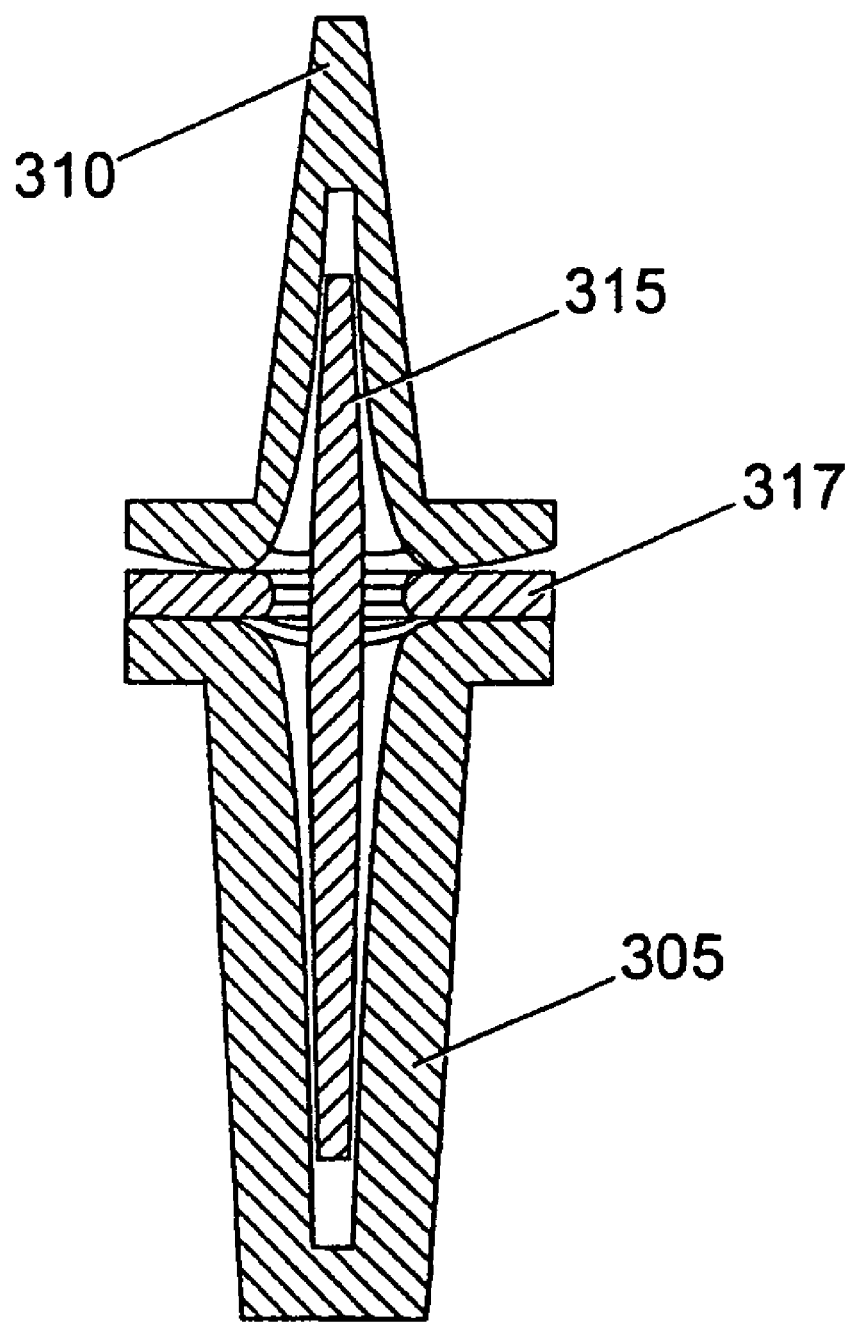
FIG. 20 is a front section view of a yet further alternative embodiment of the invention.

FIG. 20 shows a further embodiment of the invention, which is similar to the FIGS. 18 and 19 embodiments; like parts have similar reference numerals, prefixed with "3". In this embodiment, the lateral clearance between flexible member 115 and the cavity formed by the bores in the first and second components 305, 310 is relatively small at the inner ends of each bore (i.e. flexible member 115 is a close lateral fit within the cavity at each end), but towards the bore mouths the diameter of each bore increases at a greater rate than the diameter of flexible member 315 to leave a wider lateral clearance with flexible member 115 at the bore mouths. The rate of change in width of each bore increases towards the bore mouth, so that the bore mouth is flared like the bell of a trumpet. In some embodiments, the flare at the bore mouth can be even more pronounced than shown in FIG. 20, with the flaring of the bore starting even further from the bore mouth. The flaring of each bore is smooth, so that the bore mouth does not have any sharp corners which could otherwise abrade and damage flexible member 315. Like the FIGS. 18 and 19 embodiments, the bore in bearing plate 317 is also chamfered so that there are no sharp corners here either.

The FIG. 20 embodiment provides the advantage that the close fit between flexible member 315 at the bore ends prevents the first and second components 305, 310 from dislocating from each other, whilst the wider fit at the bore mouths helps prevent excessive wear on flexible member 315.

The invention claimed is:

1. An implantable replacement joint comprising a first component for attachment to a first bone portion; a second component for attachment to a second bone portion; and a flexible component extending between the first and second components;
    wherein each of the first and second components has a respective bore and the flexible component is received within a cavity formed by the bores of the first and second components;
    wherein the flexible component is freely-floating within the cavity;
    wherein the cavity formed by the bores in the first and second components is longer than the flexible component so that the flexible component can move axially within the cavity; and
    wherein the flexible component is free to move laterally and rotationally within the cavity.

2. A replacement joint as claimed in claim 1, wherein the first and second bone components are adapted to engage first and second bone portions located on opposite sides of a joint.

3. A replacement joint as claimed in claim 1, adapted to replace a joint selected from the group consisting of wrists, fingers, toes, knees and elbows.

4. A replacement joint as claimed in claim 1, wherein the first and second components are adapted to be anchored within cavities in the respective first and second bone portions.

5. A replacement joint as claimed in claim 4, wherein the first and second components are shaped to be an interference fit within the respective first and second bone portions.

6. A replacement joint as claimed in claim 4, wherein the first and second components have formations on their outer surfaces to engage the inner surfaces of the cavities in the first and second bone portions.

7. A replacement joint as claimed in claim 1, wherein the first and second components have bearing surfaces that articulate against one another when the device is made up.

8. A replacement joint as claimed in claim 7, wherein the flexible component and the bores in the first and second components extend through the bearing surfaces.

9. A replacement joint as claimed in claim 7, wherein the bearing surfaces are arcuate to promote pivotal movements of the first and second components relative to one another.

10. A replacement joint as claimed in claim 7, wherein a bearing plate is provided between the bearing surfaces of the first and second components.

11. A replacement joint as claimed in claim 10, wherein the bearing plate is formed from a material selected from the group consisting of metal and ceramics.

12. A replacement joint as claimed in claim 10, wherein the bearing plate is of a different material from the first and second components.

13. A replacement joint as claimed in claim 10, wherein the bearing plate has two pivot points, and the first and second components are adapted to pivot on opposite faces of the bearing plate.

14. A replacement joint as claimed in claim 10, wherein the bearing plate has extensions that limit the movement of at least one of the first component and the second component relative to the bearing plate.

15. A replacement joint as claimed in claim 1, wherein the first component is pivotable relative to the second component around at least one axis.

16. A replacement joint as claimed in claim 15, wherein the at least one pivot axis is movable relative to the replacement joint.

17. A replacement joint as claimed in claim 1, wherein the first component is pivotable relative to the second component around more than one axis.

18. A replacement joint as claimed in claim 17, wherein the first and second components are pivotable relative to each other around two perpendicular axes.

19. A replacement joint as claimed in claim 1, wherein the first and second components are made from a relatively harder material than the flexible component.

20. A replacement joint as claimed in claim 1, wherein the first and second components are made from a material selected from the group consisting of stainless steel, metal alloys, plastics materials, ceramics and carbon fibre composites.

21. A replacement joint as claimed in claim 1, wherein the flexible component is resilient.

22. A replacement joint as claimed in claim 1, wherein the flexible component comprises a material having inherent flexibility.

23. A replacement joint as claimed in claim 22, wherein the flexible component is made from a material selected from the group consisting of silicone and polyurethane.

24. A replacement joint comprising a first component for attachment to a first bone portion; a second component for attachment to a second bone portion; and a flexible component extending between the first and second components;
    wherein each of the first and second components has a respective bore and the flexible component is received within a cavity formed by the bores of the first and second components, and wherein the first and second components have bearing surfaces that articulate against one another when the device is assembled;
    wherein the flexible component is freely-floating within the cavity;
    wherein the cavity formed by the bores in the first and second components is longer than the flexible component so that the flexible component can move axially within the cavity;
    wherein the flexible component is free to move laterally and rotationally within the cavity, and
    wherein the bearing surface of the first component is convex along a first axis and the bearing surface of the second component is convex along a second axis, the first and second axes being mutually perpendicular to promote pivotal movements of the first and second components relative to one another.

25. An implantable replacement joint comprising a first component for attachment to a first bone portion; a second component for attachment to a second bone portion; and a flexible component extending between the first and second components;
    wherein each of the first and second components has a respective bore and the flexible component is received within a cavity formed by the bores of the first and second components;
    wherein the flexible component is freely-floating within the cavity;
    wherein the flexible component is free to move axially, laterally and rotationally within the cavity; and wherein the first and second components have bearing surfaces that articulate against one another when the device is made up.

26. An implantable replacement joint comprising a first component for attachment to a first bone portion; a second component for attachment to a second bone portion; and a flexible component extending between the first and second components;

wherein each of the first and second components has a respective bore and the flexible component is received within a cavity formed by the bores of the first and second components;

wherein the flexible component is freely-floating within the cavity; and wherein the cavity formed by the bores in the first and second components is longer than the flexible component so that the flexible member can move axially within the cavity.

* * * * *